United States Patent [19]

Sonner

[11] Patent Number: 4,956,130

[45] Date of Patent: Sep. 11, 1990

[54] METHOD OF MAKING DENTURES

[76] Inventor: Lowell F. Sonner, 2100 Superior, Elkhart, Ind. 46516

[21] Appl. No.: 272,851

[22] Filed: Nov. 21, 1918

[51] Int. Cl.$^5$ .............................................. A61C 13/10
[52] U.S. Cl. ...................................... 264/18; 433/199.1
[58] Field of Search ............................ 264/16, 17, 18; 433/167, 171, 199.1

[56] References Cited

FOREIGN PATENT DOCUMENTS 652591 11/1962 Canada .

OTHER PUBLICATIONS

"Methods of Producing More Lifelike Dentures, Including the Preparation and Processing of Acrylic Resins", by Walter J. Pryor, Journal of American Dental Association, Jun. 1941, pp. 894–902.

Primary Examiner—James Lowe
Assistant Examiner—Christopher A. Fiorilla
Attorney, Agent, or Firm—Thomas J. Dodd

[57] ABSTRACT

A method of making lifelike dentures which includes the characterization of an outer layer of the gum and soft tissue. Several different colored polymeric powders ranging from off-white to dark pink are applied to a surface of the denture mold cavity and characterized by a polymerizable liquid or heat curable curing agent. The method produces a denture whose gums gradually deepen in color farther from the teeth to produce a lifelike denture.

7 Claims, No Drawings

METHOD OF MAKING DENTURES

BACKGROUND OF THE INVENTION

This invention relates to a method of making dentures and will have application to a method of making a more lifelike appearing denture.

Current methods of forming dentures involve the setting of artificial teeth in a mold, then pouring dental colloid or a solution of stone material into the flask and allowing it to harden. The cavity created by elimination of wax is then filled with a pink colored material to allow the soft tissue parts to take on a natural looking appearance.

Unfortunately, human gums do not possess a uniform pink color which renders the basic process outlined above ineffective in creating a lifelike denture. Some denture forming laboratories have attempted to blanch the gum area just above the teeth after hardening to simulate a lifelike looking gum but have proven ineffectual for the most part.

SUMMARY OF THE INVENTION

The denture forming method of this invention involves characterization of the artificial gum tissue prior to hardening. Three layers of outer artificial tissue are formed by individually characterizing each layer of the tissue which will be exposed when the denture wearer opens his mouth. The base material is then poured into the mold after application of the outer layer. After hardening of the base, the denture is removed and the color blending lends a lifelike appearance to the formed denture.

Accordingly, it is an object of this invention to provide for a method of making a lifelike appearing denture.

Another object of this invention is to provide for a method of forming a denture which produces graduated color in the soft tissues surrounding the teeth.

Other objects will become apparent upon a reading of the following description.

DETAILED DESCRIPTION OF THE INVENTION

The preferred method illustrated below is not intended to be exhaustive or to limit the method to those precise steps or ingredients. It has been chosen to outline the general principles of the method, so that others skilled in the art might successfully practice the method.

The denture forming method of this invention is essentially a multiple phase process which begins with the forming of artificial teeth from conventional materials and aligning the teeth in a mold of the individual patient's mouth. The teeth and the mold are then placed in a flask and dental colloid gel or dental stone is poured into the flask and allowed to cure. The mold is then removed from the flask to expose the bottom of the artificial teeth properly positioned and set in the colloid or stone. Up to this point, the formation of the denture has followed conventional procedures and will not be described further.

After the mold is formed, formation of the gums and other soft tissue begins. In the conventional process, a mixture of heat curable liquid or gel and pink or red dental powder is poured into the flask and cured, with the imprint left by the mold serving to define the shape of the gums and palate. The method of this invention includes a four step process in forming the gum and soft tissue. First, a small quantity of gingival toner powder is positioned immediately adjacent to the artificial teeth against the colloid or stone mold and a curing agent is applied to the toner to allow rapid formation of a layer of artificial tissue. The gingival toner is a powdery whitish polymer used in the art and may be obtained from Dentsply International of York, Pa. The curing agent may consist of any liquid self-polymerizing or heat cure monomer. The curing agent may be obtained from Fricke Dental Manufacturing Co. of Villa Park, Ill. under the tradename Crosslink Color Stable SEL Curing (or Heat Cure) Monomer.

Second, a layer of a mixed colored toner powder is dispensed against the mold adjacent to the layer of the previously dispensed gingival toner. The curing agent above mentioned is applied to the mixed colored toner to allow formation of the second outer layer. The mixed colored toner is preferably of a pinkish shade and may consist of a mixture of about 80 parts of a pinkish whit powder sold under the tradename OP 10-3 by Astron Dental Corp. of Wheeling, Ill. and 15 parts of a deeper pink toner sold under the tradename No. 25 Gum Red Tint by Lux-It Acrylic Manufacturing Co. of Kansas City, Mo.

Third, a layer of deeper pink toner is dispensed against the mold adjacent the previously dispensed layer of mixed color toner and the curing agent applied to form the upper gum outer layer. The deeper pink toner is preferably pure No. 25 Gum Red Tint, identified above. Finally, the flask is closed and a base material, preferably a solution of the deeper pink toner and curing agent is packed, injected or poured into the flask to form the base material for the gums and palate. The base material in the flask is then cured by heat or other conventional means. When the completed denture is removed from the flask and the mold, the exposed gum tissue resembles a natural human gum with the lighter hued pinkish-white layer closest to the teeth which gradually darkens farther from the teeth to the upper gum line. The denture simulates the lightening of a natural gum due to the pressure exerted by the seated teeth in the gum tissue, and its darkening to a more or less full pink away from the zone of influence of tooth pressure.

It should be understood that the powders identified above do not constitute the entire range of products usable in forming the denture. Any powdered or liquid material capable of polymerization and possessing the color attributes above identified may be used efficiently in producing a lifelike denture without departing from the spirit and bounds of this invention according to the following claims.

I claim:

1. A method of forming a denture comprising the steps of:
   (a) forming a plurality of false teeth and arranging said teeth in a mold which defines a mold cavity approximating the configuration of a patient's gums and soft mouth tissue;
   (b) applying a gingival tone dental polymer to said mold cavity at a surface thereof adjacent said false teeth;
   (c) applying a liquid self-polymerizing curing agent to said gingival tone polymer to characterize said gingival tone polymer;

(d) applying a generally pink hued dental polymer to said mold cavity surface adjacent said gingival tone polymer;
(e) characterizing said pink hued dental polymer by applying said liquid self-polymerizing curing agent to the pink hued dental polymer; and
(f) filling the remainder of said mold cavity with said pink hued dental polymer and curing agent to form a base, and allowing said base to cure.

2. The method of claim 1 wherein said curing agent is a color stable polymerizable liquid monomer and said gingival tone polymer is applied in powder form.

3. A method of forming a denture comprising the steps of:
   (a) forming a plurality of false teeth and arranging said teeth in a mold which defines a mold cavity approximating the configuration of a patient's gums and soft mouth tissue;
   (b) applying gingival tone dental polymer to said mold cavity at a surface thereof adjacent said false teeth;
   (c) characterizing said gingival tone polymer by applying a liquid self-polymerizing curing agent to the gingival tone polymer;
   (d) applying a light hued pink polymer to said mold cavity surface adjacent said gingival tone polymer;
   (e) characterizing said light hued pink polymer by applying said liquid self-polymerizing curing agent to said light hued pink polymer;
   (f) applying a dark pink hued polymer to said mold cavity surface adjacent said light pink hued polymer;
   (g) characterizing said dark pink hued polymer by applying said curing agent thereto; and
   (h) filling the remainder of the mold cavity with a mixture of said dark pink hued polymer and curing agent to form a base and curing said base.

4. The method of claim 3 wherein said light hued pink polymer is formed of a mixture of a light pink polymeric dental powder and said pink hued polymer wherein a gradual color graduation from said teeth to an outer periphery of said mold is achieved.

5. The method of claim 3 wherein said curing agent is a color stable polymerizable monomer and said gingival tone polymer is applied to said mold cavity surface in powder form.

6. The method of claim 5 wherein said light hued pink polymer and said pink hued polymer are applied to said mold cavity surface in powder form.

7. The method of claim 6 wherein step (f) includes filling the mold cavity with a solution of said pink hued polymer and said curing agent.

* * * * *